United States Patent [19]

Greve et al.

[11] Patent Number: 4,859,663
[45] Date of Patent: Aug. 22, 1989

[54] MULTIPLY SUBSTITUTED PYRIDINE 1-OXIDE COMPOUNDS WHICH ARE USEFUL IN TREATING BRAIN DISORDERS

[75] Inventors: Wilfried Greve, Rödermark; Ulrich Elben, Wiesbaden; Karl Rudolph, Kelkheim; Ursula Schindler, Mörfelden-Walldorf, all of Fed. Rep. of Germany

[73] Assignee: Hoechst Aktiengesellschaft, Frankfurt am Main, Fed. Rep. of Germany

[21] Appl. No.: 942,385

[22] PCT Filed: Apr. 10, 1986

[86] PCT No.: PCT/EP86/00211
§ 371 Date: Dec. 16, 1986
§ 102(e) Date: Dec. 16, 1986

[87] PCT Pub. No.: WO86/06067
PCT Pub. Date: Oct. 23, 1986

[30] Foreign Application Priority Data
Apr. 18, 1985 [DE] Fed. Rep. of Germany ....... 3514073

[51] Int. Cl.$^4$ ..................... A61K 31/55; C07D 213/89
[52] U.S. Cl. ..................... 514/212; 546/193; 546/281; 546/289; 546/297; 546/304; 546/307; 546/310; 546/312; 544/58.6; 544/60; 544/124; 544/360; 540/597; 540/604; 514/222.2; 514/227.8; 514/252; 514/318; 514/343; 514/352; 514/355; 514/344
[58] Field of Search ............... 546/193, 281, 289, 297, 546/304, 307, 310, 312; 544/60, 124, 360; 540/597, 604; 514/212, 222, 227, 255, 318, 343, 344, 352, 355, 222.2, 227.8, 252

[56] References Cited
U.S. PATENT DOCUMENTS

| | | | |
|---|---|---|---|
| 3,454,587 | 7/1969 | Littell et al. | 546/310 |
| 3,495,969 | 2/1970 | Driscoll | 546/193 |
| 3,547,935 | 12/1970 | Diehl et al. | 546/312 |
| 4,067,874 | 1/1978 | Ursprung | 546/193 |
| 4,115,396 | 9/1978 | Ursprung | 546/304 |
| 4,122,264 | 10/1978 | Ursprung | 544/124 |
| 4,289,765 | 9/1981 | Greve et al. | 514/211 |

FOREIGN PATENT DOCUMENTS

| | | | |
|---|---|---|---|
| 2235746 | 2/1973 | Fed. Rep. of Germany | 546/290 |
| 2708058 | 8/1978 | Fed. Rep. of Germany | 546/269 |
| 2900504 | 7/1980 | Fed. Rep. of Germany | 514/211 |
| 6604123 | 11/1966 | Netherlands | 546/290 |
| 1542605 | 3/1979 | United Kingdom | 546/290 |

OTHER PUBLICATIONS

Arznieum.-Forsch. (Drug. Res.) 24, No. 12 (1974), pp. 1964-1970.

Patents Abstracts of Japan, vol. 8, No. 260, 1984, Pat. No. 58-13201.
German Search Report.

Primary Examiner—Richard A. Schwartz
Assistant Examiner—Zinna Northington
Attorney, Agent, or Firm—Finnegan, Henderson, Farabow, Garrett & Dunner

[57] ABSTRACT

Multiply substituted pyridine 1-oxides of the formula I

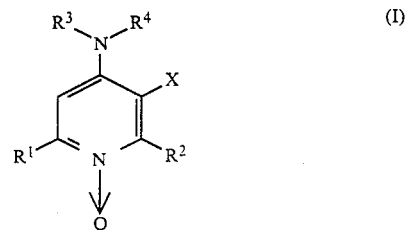

in which
$R^1$ and $R^2$ are, in each case, identical or different and represent alkyl having 1 to 6 carbon atoms,
$R^3$ denotes hydrogen, and
$R^4$ denotes mercaptoalkyl having up to 4 carbon atoms, or
$R^3$ and $R^4$ form, together with the nitrogen atom in the 4-position, a five- to seven-membered saturated heterocyclic ring which has up to 2 heteroatoms, the second heteroatom being oxygen, sulfur which can carry up to two oxygen atoms, or nitrogen in the form of the $NR^6$ group, in which $R^6$ is hydrogen, alkyl having up to 2 carbon atoms, phenylalkyl having up to 2 carbon atoms in the alkyl moiety or phenyl, and the phenyl rings in the two latter radicals can carry up to two identical or different substituents from the group comprising halogen and methoxy, and which ring is unsubstituted or carries up to two identical or different substituents from the group comprising hydroxy and alkyl having up to 2 carbon atoms, and
X denotes the cyano or nitro group the or the group —CO—$R^5$, in which $R^5$ represents the amino, hydroxyl or an alkoxy group having up to 4 carbon atoms,
and the physiologically tolerated salts of these compounds, and medicaments containing or composed of these compounds.

The invention further relates to a process for the preparation of the multiply substituted pyridine 1-oxides of the formula I, and to their use for the preparation of medicaments whcih are intended for the prevention and treatment of brain disorders caused by vascular and degenerative factors.

13 Claims, No Drawings

MULTIPLY SUBSTITUTED PYRIDINE 1-OXIDE COMPOUNDS WHICH ARE USEFUL IN TREATING BRAIN DISORDERS

The preparation of substituted 3-nitro(and cyano)-4-aminopyridines which have bronchospasmolytic activity is described in German Offenlegungsschrift 2,900,504. However, the corresponding pyridine 1-oxides are not described in this printed publication. U.S. Patent 3,547,935 relates to 3-nitropyridines which have herbicidal activity, the definition of substituents to describe the general structural formula embracing, inter alia, 2,6-dialkyl-4-di-alkylamino-3-nitropyridine 1-oxides without, however, compounds of this type being disclosed by means of examples or by naming. Furthermore, the two German Offenlegungsschriften 3,209,274 and 3,209,276 describe 3-pyridinecarboxylic esters and 3,5-pyridinedicarboxylic esters having a substituent, bonded via a carbon atom, in the 4position, which are said to be suitable for the treatment of disorders caused by ischemia and/or hypoxia. Furthermore, the literature discloses 3-phenoxypyridine and derivatives (J.Med.Chem. 24, 346 11981) and Belgian Patent 876,389) and 2-cyano-3-phenoxypyridine 1-oxides (sic) (U.S. Pat. Nos. 4,187,379 and 4,229,457), which are attributed with antiamnesic properties.

It has now been found, surprisingly, that by the introduction of an oxygen atom in the 1-position of pyridine derivatives of the structural type described in German Offenlegungsschrift 2,900,504 there are obtained new compounds which no longer show bronchospasmolytic activity but have other valuable pharmacological properties. Of these, the principal is a pronounced cerebroprotective action which is accompanied by effects inhibiting platelet aggregation and antiedematous effects. The compounds according to the invention are in this respect considerably superior to the compounds of the other literature citations which have been mentioned as the state of the art, of which representative agents have likewise been included in the pharmacological investigation, since the known compounds have proved to be considerably less active or even inactive. Furthermore, the compounds according to the invention are also suitable as starting materials for the preparation of other valuable drugs.

Consequently, the present invention relates to new, multiply substituted pyridine 1-oxides, including the relevant salts, to a process for their preparation, to medicaments containing them, in particular those which allow prophylactic and curative treatment of brain disorders caused by vascular and degenerative factors, and to the use of the pyridine 1-oxides of the formula I and/or of the salts for the preparation of medicaments which are meant for the prevention and treatment of brain disorders caused by vascular and degenerative factors.

Thus, the subject matter is the substituted pyridine 1oxides of the formula I (see claim 1) in which
$R^1$ and $R^2$ are, in each case, identical or different and represent straight-chain or branched alkyl having 1 to 6, preferably having 1 to 3, carbon atoms, in particular methyl,
$R^3$ denotes hydrogen, and
$R^4$ denotes mercaptoalkyl having up to 4 carbon atoms, or
$R^3$ and $R^4$ form, together with the nitrogen atom in the 4-position, a five- to seven-membered saturated heterocyclic ring which has up to 2 heteroatoms, the second heteroatom being oxygen, sulfur which can carry up to two oxygen atoms, or nitrogen in the form of the $NR^6$ group, in which $R^6$ is hydrogen, alkyl having up to 2 carbon atoms, phenylalkyl having up to 2 carbon atoms in the alkyl moiety or phenyl, and the phenyl rings in the two latter radicals can carry up to two identical or different substituents from the group comprising halogen and methoxy, and which ring is unsubstituted or carries up to two identical or different substituents from the group comprising hydroxy and alkyl having up to 2 carbon atoms, and
X denotes the cyano or nitro group or the group —CO-$R^5$, in which $R^5$ represents the amino, hydroxyl or an alkoxy group having 1 to 4 carbon atoms,
and the physiologically tolerated salts of these compounds.

$R^1$ and $R^2$ together preferably do not contain more than 8, and in particular not more than 6, carbon atoms. In $R^4$ the mercaptoalkyl radical preferably contains up to 2 carbon atoms. The alkyl radical in the ring formed of $R^3$ and $R^4$ and in the phenylalkyl radical can contain one or two carbon atoms, and the halogen on the phenyl ring can be, in particular, fluorine, chlorine or bromine.

Preferred compounds of the formula I, and their salts, are those in which $R^1$ and $R^2$ each represent methyl, X denotes the cyano or nitro group, and the group $NR^3R^4$ represents a heterocyclic ring which has at least 4 carbon atoms, preferably a thiomorpholine, morpholine, pyrrolidine, piperidine, hexamethyleneimine, piperazine or homopiperazine ring, and which is unsubstituted or substituted by one alkyl having up to 2 carbon atoms, or represents a 4-phenylpiperazine radical which is unsubstituted or substituted in the phenyl nucleus by one halogen.

Among these compounds, in turn those of the formula I, and their salts, to which attention is particularly drawn are those in which $R^1$ and $R^2$ each denote methyl, X denotes the cyano group, and $NR^3R^4$ denotes the thiomorpholine, piperidine or hexamethyleneimine ring, and especially 3-cyano-2,6-dimethyl-4-(4-thiomorpholinyl)-pyridine 1-oxide.

The compounds of the formula I are new and, as mentioned in the introduction, have valuable pharmacological, especially cerebroprotective, properties.

The invention furthermore relates to a process for the preparation of the pyridine 1-oxides according to formula I and of their physiologically tolerated salts, which comprises
(a) oxidation of a compound of the formula II

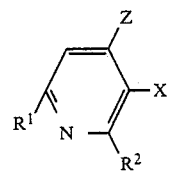

to a pyridine 1-oxide of the formula III

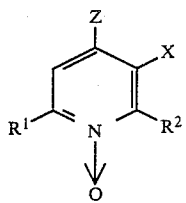

and then reaction of the latter wih an amine of the formula HNR³R⁴ (IV) to give a pyridine 1oxide of the formula (I), R¹ to R⁴ and X having the above-mentioned meanings and Z representing a halogen atom, in particular chlorine or bromine, or (b) oxidation of a compound of the formula V

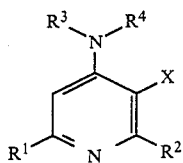

in which R¹ to R⁴ and X have the abovementioned meanings, to a pyridine 1-oxide of the formula I, any thioether group contained in the radical —NR³R⁴ simultaneously also being oxidized, and isolation of the product obtained according to a) or (b) or (c) for the preparation of a compound of the formula I in which the NR³R⁴ group contains a sulfoxy or sulfone group, subsequent oxidation, where appropriate stepwise, of the sulfur in the thioether compound obtained by process (a), or (d) for the preparation of a compound of the formula I in which X represents the radical —CONH₂, hydrolysis of a 3-cyano compound of the formula I to the amide, or reaction of a 3-carboxylic ester of the formula I with ammonia, or e) for the preparation of a compound of the formula I in which X denotes the carboxyl group, hydrolysis of a 3-carboxylic ester of the formula I, the compounds of the formula I being either isolated in the free form or forming physiologically tolerated salts with suitable, i.e. physiologically tolerated, acids or, in the case where X represents a COOH group, with suitable, i.e. physiologically tolerated, bases.

Examples of acids suitable for the preparation of acid addition salts are mineral acids such as sulfuric or phosphoric acid or hydrohalic acids, in particular hydrochloric acid, and organic acids such as monobasic to tribasic carboxylic acids, for example acetic, lactic, maleic, fumaric, oxalic, tartaric, citric or gluconic acid, or other physiologically tolerated acids, such as sulfonic acids, for example p-toluenesulfonic, methanesulfonic, trifluoromethylsulfonic and cyclohexylamidosulfonic acid.

The compounds of the formula I in which X represents a carboxyl group can also form with basic reagents, such as hydroxides, alcoholates, carbonates and bicarbonates stable alkali metal and alkaline earth metal salts which are soluble in water.

Most of the starting materials of the formulae II and V are known from the literature or can readily be prepared by methods described in the literature.

Examples of suitable compounds II which may be mentioned are the symmetrical 2,6-dialkyl-4-halogeno-3-nitropyridines such as 4-chloro-2,6-dimethyl-3-nitropyridine (P. Nantka-Namirski, Acta Polon. Pharm. 18, 449 (1961)) and 4-chloro-2,6-dipropyl-3-nitropyridine, both of which can be obtained from acylacetic esters via the 6-alkyl-3-acyl-2,3-dihydro-2,4-dioxopyrans by reaction with ammonia followed by nitration in the 3-position and halogenation of the 4-position; also suitable are 2,6-dialkyl-3-cyano-4-halogenopyridines such as 4-chloro-3-cyano-2,6-dimethylpyridine (T. Kato et al., Yakugaku Zasshi 91, 740 (1971)) and 4-chloro-3-cyano-2,6-dipropylpyridine, and 2,6-di- alkyl-4-halogenopyridine-3-carboxylic esters, such as ethyl 2,6-dimethyl-4-chloropyridine-3-carboxylate, which can be prepared by condensation of 3-alkyl-3-aminoacrylic esters with phosphorus oxytrichloride (J.N. Phillips et al., Angew. Chem. 88, 539 (1976)) or with acylacetic esters (Czechoslovak. Patent 147,252; CA. 78, 159448 j), and their unsymmetrical 2,6-dialkyl derivatives, such as the 3-substituted 2-hexyl-6-methyl- and 6-hexyl-2-methyl-4-chloropyridines, which can be synthesized by, for example, reaction of corresponding 3-alkyl-3-aminoacrylic esters with diketene (T. Kato et al., Yakugaku Zasshi 91, 740 (1971)) or any desired acylacetic esters, followed by hydrolysis, decarboxylation, nitration, separation of isomers and halogenation. Furthermore, the compounds of the formula II in which X represents the cyano group can also be obtained from the corresponding nitro compounds by reduction of the nitro group to the amino group, diazotization thereof and subsequent nucleophilic exchange by the cyano group (C. Rath, Liebigs Ann. Chem. 486, 95 (1931)), advantageously with copper(I) salt catalysis. This sequence of reactions can be applied to the 3-nitropyridine 1-oxides of the formula III and thus permits their conversion in this case too into the corresponding 3-cyanopyridine 1-oxides.

Most of the starting compounds V are disclosed in German Offenlegungsschrift 2,900,504 or can readily be prepared in an analogous manner by reaction of the 3-substituted 2,6-dialkyl-4-halogenopyridines II with the amines IV.

Examples of agents suitable for the N-oxidation both of the pyridine derivatives II to the intermediates III, in accordance with process (a), and of the substituted 4-aminopyridines V to the compounds I according to the invention, in accordance with process b), are hydrogen peroxide, and perborates, but preferably organic percarboxylic acids, such as performic acid, peracetic acid, trifluoroperacetic acid, monopermaleic, monopersuccinic, perbenzoic, 4-nitroperbenzoic, monoperphthalic and, in particular, 3-chloroperbenzoic acid. However, electrochemical oxidation is also possible.

The reaction with the percarboxylic acids is advantageously carried out in a solvent or dispersant which is inert towards the participants in the reaction and which, experience has shown, exerts a considerable effect on the rate of reaction. In general, the reaction is carried out under atmospheric pressure, although it is likewise possible to employ increased or reduced pressure. Since solvents or dispersants which can form hydrogen bonds with the percarboxylic acid generally reduce the rate of reaction, aromatic hydrocarbons, such as benzene, toluene or xylenes, and halogenated hydrocarbons, such as dichloromethane, chloroform or tetrachloromethane, or mixtures thereof, are frequently preferred to ethers, such as diethyl ether, dioxane, tetrahydrofuran or ethylene glycol dimethyl ether, alcohols, esters and carboxylic acids. The reaction is usually carried out at temperatures between +10° C. and the boiling point of the particular solvent, i.e. of the reaction medium, preferably at 20° to 70° C., it being possible for the reaction time to extend up to several hours. The percarboxylic acids are usually used in the isolated form for the reaction, but it is also possible for them to be generated in situ in the reaction mixture, for example from the corresponding carboxylic acid and hydrogen peroxide.

The reaction of the pyridine 1-oxides III which are halogenated in the 4-position with the amines IV in accordance with process (a) is also advantageously carried out in a solvent or dispersant which is inert towards the reactants. Examples which are suitable for this purpose are alcohols, such as methanol, ethanol, isopropanol, n-propanol, the various butanols and mixtures thereof, as well as their mixtures with ethers, such as tetrahydrofuran and dioxane, or hydrocarbons, such as benzene, toluene and xylene, as well as aprotic solvents, such as pyridine, dimethylformamide, dimethylacetamide, dimethyl sulfoxide and hexamethylphosphoric triamide.

At least twice the molar amount of the amine is advantageously used in the reaction of the compounds III with the amines IV; it is also possible to use equimolar amounts of the two reactants, but it is then advisable to add an acid-binding agent, for example an alkali metal or alkaline earth metal hydroxide or carbonate, or an organic base such as triethylamine, in at least stoichiometric amount. The reaction is generally carried out at temperatures between 0° C. and the boiling point of the particular solvent, i.e. of the reaction medium, preferably between 20° and 100° C., it being possible for the reaction time to be up to several hours.

Examples of suitable amines IV are pyrrolidine, piperidine, 4-hydroxypiperidine, hexamethyleneimine, morpholine, thiomorpholine, 2-methylthiomorpholine, 2-mercaptoethyLamine, piperazine, homopiperazine and the monosubstituted piperazines, such as 1-methyl-, 1-benzyl-, 1-phenyl-, 1-(4-methoxyphenyl)-, 1-(3-chlorophenyl)- or 1-(4-fluoro-phenyl)-piperazine, as well as thiomorpholine 1-oxide and 1,1-dioxide.

The oxidation of compounds according to the invention, of the formula I, with an $NR^3R^4$ radical containing thioether groups to sulfoxides or sulfones according to process (c) is carried out by customary methods, for example with nitric acid, elementary chlorine, perborates, the abovementioned percarboxylic acids, and hydrogen peroxide, but preferably with periodates, such as tetrabutylammonium periodate and sodium metaperiodate, for the preparation of sulfoxides. In principle, the same oxidizing agents are suitable for the preparation of sulfones, but nitric acid, chlorine and, in particular, hydrogen peroxide are preferred. Water is preferably used as the diluent for this. In addition, it frequently proves beneficial for this to add a carboxylic acid, such as acetic acid. The reaction temperatures are, as a rule, between −20° and +100° C., preferably between 0° and 80° C.

Any conversion of the cyano compounds and carboxylic esters of the formula I, according to the invention, into the relevant amides of the formula I according to process (d), and of the carboxylic esters according to the invention into the carboxylic acids of the formula I in accordance with process (e), is carried out in a customary manner. Thus, the hydrolysis of the cyano compounds to the amides can be carried out under acid or, preferably, alkaline, in particular strongly alkaline, conditions, the process mainly being carried out in lower alcohols, ethers or, in particular, water, with the addition of alkaline reagents, preferably alkali metal hydroxides, such as sodium or potassium hydroxide, at temperatures between 20° and the boiling point of the particular solvent. The aminolysis of the carboxylic esters according to the invention with ammonia to give the amides of the formula I is also advantageously carried out in a solvent which is inert towards the reactants, preferably an alcohol, such as methanol, ethanol or isopropanol, it being advisable to employ elevated pressures and temperatures between 100° and 200° C. The hydrolysis of the carboxylic esters according to the invention to the acids of the formula I can likewise be carried out under either acid or alkaline conditions. However, alkaline hydrolysis is preferred and is advantageously carried out in a solvent such as water, an ether, ketone or lower alcohol, preferably ethylene glycol, in the presence of alkaline reagents, preferably alkali metal hydroxides or carbonates, in particular sodium or potassium hydroxide, where appropriate at elevated temperatures.

The pyridine 1-oxides of the formula I, according to the invention, and their physiologically tolerated salts can, because of their hharmacological properties, be used as medicaments, in particular as medicaments for the prophylactic and curative treatment of brain disorders caused by vascular and degenerative factors, and they are administered either alone, for example in the form of microcapsules, in mixtures with one another, or in combination with suitable auxiliaries and/or vehicles.

Thus the invention also relates to medicaments which contain or are composed of at least one compound of the formula I, where appropriate in the form of one of its physiologically tolerated salts, as active compound, and are a genuine enrichment of pharmacy.

In general, the medicaments according to the invention are administered orally or parenterally; in principle, however, rectal or percutaneous administration is also possible. Examples of suitable solid or Liquid pharmaceutical presentations are granules, powders, tablets, coated tablets, (micro)capsules, suppositories, syrups, emulsions, suspensions, aerosols, drops or injectable solutions in ampule form, the desiccated ampule also being included as a special presentation, as well as products with protracted release of active compound, in whose manufacture use is usually made of auxiliaries, such as vehicles, disintegrants, binders, coating and swelling agents, release agents or lubricants, flavorings, sweetening agents, buffer substances, antioxidants or solubilizers. Examples of auxiliaries which are frequently used and which may be mentioned are magnesium carbonate, titanium dioxide, lactose, mannitol and other sugars, talc, lactalbumin, gelatin, starch, vitamins, cellulose and its derivatives, animal and vegetable oils, polyethylene glycols, and solvents such as, for example, sterile water, alcohols, glycerol and other polyhydric alcohols.

It is preferable for the pharmaceutical products to be manufactured and administered in dosage units, each unit containing as active ingredient a defined dose of a compound according to formula I, where appropriate in the form of one of its physiologically tolerated salts. In the case of solid dosage units such as tablets, capsules and suppositories, this dose can be up to 1,000 mg, but is preferably 100 to 300 mg, and in the case of injection solutions in ampule form, it can be up to 200 mg, but is preferably 20 to 100 mg.

The daily doses indicated for the treatment of an adult patient are, depending on the activity of the compounds according to formula I and of their salts in humans, from 100 to 2,000 mg of active compound, preferably 300 to 900 mg, on oral administration, and from 5 to 500 mg, preferably 20 to 200 mg, on intravenous administration. However, in some circumstances higher or lower daily doses may be advisable. The administration of the daily dose can be carried out either by a single administration in the form of a single dosage unit or of several smaller dosage units, or by multiple administration of divided doses at particular intervals.

Finally, in the manufacture of the abovementioned pharmaceutical presentations, the pyridine 1-oxides of the formula I, and their salts, can also be formulated together with other suitable active compounds, for example antihypertensives, including β-receptor and calcium-channel blockers, agents having antianginal and positive inotropic actions, diuretics, sedatives, antidepressants, and antihyperlipidemic, antithrombotic and vasotherapeutic agents.

EXAMPLES:

The structure of the compounds which are described below was proven by elemental analysis and IR and $^1$H-NMR spectra.

(1)

3-Cyano-2,6-dimethyl-4-(4-thiomorpholinyl)pyridine 1-oxide hydrochloride:

a) 50 g (0.3 mol) of 4-chloro-3-cyano-2,6-dimethylpyridine were dissolved in 1 L of dichloromethane and, at room temperature, 130 g (0.6 mol) of 80% pure m-chloroperoxybenzoic acid were added in portions, and the mixture was stirred overnight and the precipitated m-chlorobenzoic acid was filtered off. Water was added to the filtrate, the pH was adjusted to 12 with solid potassium hydroxide, and the two phases were shaken together to extract. The dichloromethane phase was separated off, dried over sodium sulfate, filtered and evaporated. 4-Chloro-3-cyano-2,6dimethylpyridine 1-oxide was obtained as a solid compound which sintered at 140° C. Yield: 49.3 g (90% of theory).

b) 49.3 g (0.27 mol) of the compound obtained above, 31.0 g (0.30 mol) of thiomorpholine and 40 ml (0.28 mol) of triethylamine were dissolved in 150 ml of methanol, and the mixture was heated to reflux under nitrogen for 10 hours. After the reaction was complete, the solvent was removed by distillation under reduced pressure, and the residue was taken up in 200 ml of dichloromethane, and 100 ml of water were added. The mixture was acidified to pH 5 with 2 N hydrochloric acid. The water phase was separated off, and the remaining dichloromethane phase was dried over sodium sulfate, filtered and evaporated to dryness under reduced pressure. The residue was recrystallized from isopropanol/water (ratio by volume 3:1). The base thus purified was dissolved in the smallest possible amount of hot ethanol, and 8 N ethanolic HCl was added. The solution was evaporated to opalescence, and crystallization was allowed to go to completion in a refrigerator.

Yield: 46.3 g (60% of theory)
$C_{12}H_{16}ClN_3SO$ (MW: 285.79); melting point 237°–239° C.
Analysis: calculated: C 50.43%, H 5.64%, Cl 12.40%, N 14.70%, S 11.22%; found: C 50.49%, H 5.72%, Cl 12.37%, N 14.70%, S 11.20%;

(2)

3-Cyano-2,6-dimethyl-4-(4-thiomorpholinyl)pyridine 1-oxide S-oxide hydrochloride:

9 g (0.03 mol) of the compound from Example 1b were dissolved in water and, at 0° C., 7.07 g (0.033 mol) of sodium periodate were added. The reaction mixture was allowed to reach room temperature and was then stirred for 20 hours, and the mixture was diluted with methanol and the precipitate which had separated out was filtered off. The aqueous phase was extracted by shaking with dichloromethane, then neutralized with sodium bicarbonate and extracted once more by shaking with dichloromethane. The latter dichloromethane phase was evaporated, and the solid residue was recrystallized from isopropanol/diisopropyl ether (ratio by volume 4:1).

Yield: 6.72 g (80% of theory)
$C_{12}H_{15}N_3O_2S$ (MW =265.34); melting point 180° C.
Analysis: calculated: C 54.32%, H 5.69%, N 15.83%, S 12.08%; found: C 54.41%, H 5.65%, N 15.75%, S 12.13%;

(3)

3-Cyano-2,6-dimethyl-4-(4-thiomorpholinyl)pyridine 1-oxide S,S-dioxide hydrochloride:

3 g (0.012 mol) of the compound from Example 1b were dissolved in 10 ml of 30% strength hydrogen peroxide and 20 ml of glacial acetic acid. This mixture was heated at 70° C. for 3 hours and, after cooling to room temperature, 100 ml of isopropanol were added, and the solution was stirred for a further 30 minutes and evaporated to dryness under reduced pressure, the residue was taken up in water and the solution was neutralized with sodium bicarbonate. The aqueous phase was extracted by shaking with dichloromethane. The dichloromethane phase was separated off and boiled with active charcoal. The solution was evaporated to dryness, and the product was converted into the hydrochloride with ethanolic HCl. It was crystallized from isopropanol.

Yield: 3.4 g (91% of theory).
$C_{12}H_{16}ClN_3O_3S$ (MW 317.80); melting point 24°6 C.
Analysis: calculated: C 45.36%, H 5,08%, Cl 11.15%, N 13.22%, S 11.08%; found: C 45.11%, H 5.19%, Cl 11.07%, N 13.01%, S 10.85%.

It was also possible to obtain the same compound in an analogous manner from the compound of Example 2.

(4)

3-Cyano-2,6-dipropyl-4-(4-thiomorpholinyl)pyridine 1-oxide hydrochloride:

14 g (0.066 mol) of 3-amino-4-chloro-2,6-dipropylpyridine were dissolved in a mixture of 9.4 g of concentrated sulfuric acid and 70 ml of water. This solution was cooled to 0° C. and a solution of 4.8 g (0.07 mol) of sodium nitrite in 14 ml of water was added dropwise. The diazonium salt solution thus obtained was allowed to run into a boiling solution of 5.9 g (0.07 mol) of copper(I) cyanide and 12.92 g (0.198 mol) of potassium cyanide in 100 ml of water. The reaction was complete after brief further heating. The reaction mixture was made strongly alkaline and was extracted with ether. The residue on evaporation of the ether phase was 6 g (0.027 mol) of crude 4-chloro-3-cyano-2,6-dipropylpyridine, which was taken up in 100 ml of dichloromethane, and 11.6 g (0.054 mol) of 80% pure m-chloroperoxybenzoic acid were added, and then the mixture was stirred at room temperature for 12 hours. The solution was filtered, extracted by shaking with saturated potassium carbonate solution, and the dichloromethane phase was evaporated. The 6 g (0.025 mol) of the pyridine 1-oxide thus obtained was reacted with 5.18 g (0.05 mol) of thiomorpholine in isopropanol as described in Example 1. It was possible to purify the resulting crude product by column chromatography on silica gel using ethyl acetate/cyclohexane (ratio by volume 4:1) as mobile phase. A yellow-colored oil was obtained, and this crystallized completely on prolonged standing.

Yield: 2.3 g (42% of theory)

$C_{16}H_{24}ClN_3OS$ (MW: 341.91); melting point 34° C.

Analysis: calculated: C 56.21, H 7.08, Cl 10.37, N 12.29, S 9.38; found: C 56.01, H 7.19, Cl 10.41, N 12.06, S 9.37.

(5) 2,6-Dimethyl-4-(4-morpholinyl)-3-nitropyridine 1-oxide: 4 g (0.016 mol) of 2,6-dimethyl-4-(4-morpholinyl)-3-nitropyridine were dissolved in 200 ml of dichloromethane, and 3.8 g (0.018 mol) of 80% pure 3-chloroperoxybenzoic acid were added. After 20 hours, the precipitate which had separated out was filtered off, the filtrate was evaporated to dryness, and the residue was extracted by shaking with a saturated potassium carbonate solution and dichloromethane. The residue on evaporation of the organic phase was recrystallized from ethanol/diisopropyl ether (ratio by volume 3:1).

Yield: 5.6 g (56% of theory)

$C_{11}H_{16}ClN_3O_4$ (MW: 289.72); melting point 189° C.

Analysis: calculated: C 45.60, H 5.57, Cl 12.23, N 14.50; found: C 45.95, H 5.64, Cl 11.98, N 14.40.

(6) 2,6-Dimethyl-4-(4-thiomorpholinyl)pyridine-3-carboxamide 1-oxide:

3 g (0.012 mol) of 3-cyano-2,6-dimethyl-4-(4-thiomorpholinyl)pyridine 1-oxide hydrochloride (from Example 1) were dissolved in 10 ml of 10 N sodium hydroxide solution, and the solution was heated under reflux for 6 hours. It was then evaporated until a precipitate formed, the mixture was cooled, and the solid was filtered off and recrystallized from methanol.

Yield: 2.5 g (78% of theory)

$C_{12}H_{17}N_3O_2S$ (MW: 267.35); melting point 285°–287° C.

Analysis: calculated: C 53.91, H 6.41, N 15.72, S 11.99; found: C 53.93, H 6.44, N 15.64, S 12.10.

(7) 2,6-Dimethyl-4-(4-thiomorpholinyl)pyridine-3-carboxylic acid 1-oxide hydrochloride:

38.2 g (0.129 mol) of ethyl 2,6-dimethyl-4-thiomorpholinylpyridine-3-carboxylate 1-oxide(see Table 1, Example 19), 10.6 g (0.189 mol) of solid potassium hydroxide and 100 ml of ethylene glycol were heated at 170° C. for 5 hours. The mixture was then diluted with water, neutralized with 6 N hydrochloric acid, and the water and ethylene glycol were removed by distillation under reduced pressure. The residue was taken up in ethanol, insolubles were removed by filtration, and the solution was boiled with active charcoal, filtered once more and ethanolic HCl was added. The mixture was evaporated to dryness, and the hydrochloride was recrystallized from methanol.

Yield: 9.6 g (24.8% of theory)

$C_{12}H_{17}ClN_2O_3S$ (MW: 304.79); melting point 222° C. (decomposition)

Analysis: calculated: C 47.29, H 5.62, Cl 11.63, N 9.19, S 10.52; Found: C 47.56, H 5.63, Cl 11.23, N 9.22, S 10.40.

The abovementioned compounds and those prepared in an analogous manner are compiled in Table 1 below.

TABLE 1

| | | | Compounds of formula I | | | |
| --- | --- | --- | --- | --- | --- | --- |
| Example | $R^1$ | $R^2$ | $-NR^3R^4$ | X | isolated as | Melting point °C. |
| 1 | $CH_3$ | $CH_3$ | 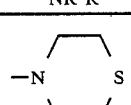 | CN | HCl | 237–239 |
| 2 | $CH_3$ | $CH_3$ | 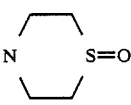 | CN | Base | 180 |
| 3 | $CH_3$ | $CH_3$ | 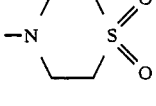 | CN | HCl | 246 |
| 4 | $C_3H_7$ | $C_3H_7$ | 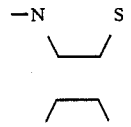 | CN | HCl | 34 |
| 5 | $CH_3$ | $CH_3$ | 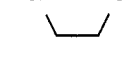 | $NO_2$ | HCl | 189 |

TABLE 1-continued

Compounds of formula I

| Example | R¹ | R² | —NR³R⁴ | X | isolated as | Melting point °C. |
|---|---|---|---|---|---|---|
| 6 | $CH_3$ | $CH_3$ | —N(CH₂CH₂)₂S (thiomorpholino) | $CONH_2$ | Base | 285–287 |
| 7 | $CH_3$ | $CH_3$ | —N(CH₂CH₂)₂S (thiomorpholino) | COOH | HCl | 222 |
| 8 | $CH_3$ | $CH_3$ | —N(CH₂CH₂)₂S (thiomorpholino) | $NO_2$ | HCl | 204–206 |
| 9 | $CH_3$ | $CH_3$ | —N(CH₂CH₂)₂O (morpholino) | CN | HCl | 245 |
| 10 | $CH_3$ | $CH_3$ | —N(CH₂CH₂)₂N—CH₃ | CN | 2 HCl × $H_2O$ | 265–267 |
| 11 | $CH_3$ | $CH_3$ | —N(CH₂CH₂CH₂)₂N—H (homopiperazine) | $NO_2$ | 2 HCl | 240 |
| 12 | $CH_3$ | $CH_3$ | —N(CH₂CH₂CH₂)₂N—H (homopiperazine) | CN | HCl | 218–220 |
| 13 | $CH_3$ | $CH_3$ | —N (pyrrolidino) | CN | HCl | 209 |
| 14 | $CH_3$ | $CH_3$ | —N (piperidino) | CN | HCl | 223 |
| 15 | $CH_3$ | $CH_3$ | —N(CH₂CH₂)₂S with $CH_3$ (2-methylthiomorpholino) | CN | HCl | 211 |
| 16 | $CH_3$ | $CH_3$ | —N(CH₂CH₂)₂N—C₆H₅ (4-phenylpiperazino) | CN | HCl | 195 |
| 17 | $CH_3$ | $CH_3$ | —N(CH₂CH₂)₂N—H (piperazino) | CN | Base | 243 |

TABLE 1-continued

Compounds of formula I

| Example | R¹ | R² | —NR³R⁴ | X | isolated as | Melting point °C. |
|---|---|---|---|---|---|---|
| 18 | CH₃ | CH₃ |  pyrrolidine | COOC₂H₅ | Base | 151 |
| 19 | CH₃ | CH₃ | 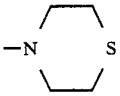 thiomorpholine | COOC₂H₅ | Base | 98 |
| 20 | CH₃ | CH₃ | 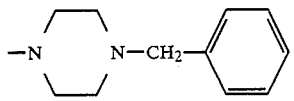 4-benzylpiperazine | CN | 2 HCl | 245 |
| 21 | CH₃ | CH₃ | 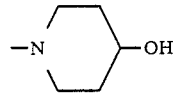 4-hydroxypiperidine | CN | Base | 191 |
| 22 | CH₃ | CH₃ | 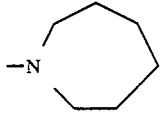 hexamethyleneimine | CN | Base | 143–144 |
| 23 | CH₃ | CH₃ | 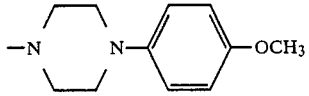 4-(4-methoxyphenyl)piperazine | NO₂ | 2 HCl | 170 |
| 24 | CH₃ | CH₃ | 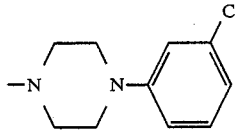 4-(3-chlorophenyl)piperazine | NO₂ | 2 HCl | 176 |
| 25 | CH₃ | CH₃ | 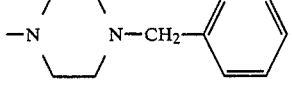 4-benzylpiperazine | NO₂ | 2 HCl × H₂O | 208 |
| 26 | CH₃ | CH₃ | 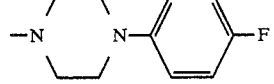 4-(4-fluorophenyl)piperazine | NO₂ | 2 HCl | 196 |
| 27 | CH₃ | CH₃ |  pyrrolidine | NO₂ | HCl | 196 |
| 28 | CH₃ | CH₃ |  piperidine | NO₂ | HCl | 171 |
| 29 | CH₃ | CH₃ | —NH—CH₂—CH₂—SH | CN | HCl | 212 |
| 30 | CH₃ | C₆H₁₃ | 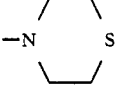 thiomorpholine | CN | HCl × H₂O | 104 |

PHARMACOLOGICAL TESTS AND RESULTS

1. Antihypoxic action

The compounds according to the invention were tested for a cerebroprotective action towards damage caused by hypoxia by means of the EEG hypoxia-tolerance test (EEG: Electroencephalogram) comparing with the most important representatives of types of compounds which belong to the state of the art. In this method, anesthetized male rats with implanted EEG electrodes are subjected to progressive hypoxia by passing nitrogen into a chamber. This results in the electrical activity of the brain being extinguished after about 2 minutes, i.e. the EEG becomes isoelectric. Immediately after the isoelectricity has occurred, the hypoxia chamber is opened whereupon, after about 60 seconds, the first EEG signals can be recorded again for untreated control animals. The criterion used for assessment of an antihypoxic action is the EEG hypoxia recovery latency period (EEG-RL), which is defined as the time from the opening of the chamber after onset of EEG silence until the first signals appear again. A substance which has a protective, i.e. antihypoxic, action results in a shortening of the EEG-RL compared with an untreated control group, and the percentage change is used to measure the activity. The compounds according to the invention were administered intraperitoneally 15 minutes before the start of hypoxia. The group size was n = 8.

2. Acute toxicity

The standard method for the determination of the $LD_{50}$ values or $LD_{50}$ ranges via the mortality occurring in Naval Medical Research Institute mice within 7 days after a single intravenous (i.v.), intraperitoneal (i.p.) or oral (p.o.) administration was used.

The results of these investigations, which demonstrate the superiority of the compounds according to the invention, of the formula I, compared with known comparison products, are compiled in Table 2.

is an agent which is frequently used for the treatment of brain disorders (S. Hoyer, Med. Prax. 79, 22–34 (1984)):

(a) Effect on the scopolamine-induced retrograde amnesia in the passive avoidance test The test arrangement comprises a light/dark box with an electrifiable mesh floor in the dark section. 90 minutes after administration of placebo and product, naive mice of the male sex are treated subcutaneously with scopolamine hydrobromide (3 mg/kg). The mice are placed in the light section of the box 5 minutes later. After transferring into the dark section they receive there an electric shock to the feet which produces an unpleasant sensation. 24 hours thereafter, each mouse is placed once in the light section of the test apparatus, and the residence time (max. 180 seconds) is measured. The residence time in this test was found to be long with animals treated with an active dose of a product and scopolamine as well as with animals not treated with scopolamine, whereas those which received only placebo and scopolamine remained only a short time. The significant action of a test substance is calculated, using a median test, by comparison with the control group. The minimal effective dose (MED) of a product is regarded as that which results in a significant action countering scopolamine.

In this test the compound from Example 1, for example, on oral administration proved, with a MED of 25 mg/kg, to be four times as effective as piracetam, for which the corresponding MED value was found to be 100 mg/kg.

(b) Gamma-butyrolactone test on the rat

It is known from the literature (L.I. Wolfson et al., J. Neurochem. 29, 777 (1977)) that gamma-butyrolactone (GBL), inter alia, induces metabolic disturbances in the brain which can be followed by changes in the EEG. The compounds of the formula I are able to antagonize this action of GBL on the EEG. Thus, for example, the compound of Example 1 showed, after intraperitoneal administration of 100 and 200 mg/kg, a strong, dose-

TABLE 2

| | Pharmacological test results | | |
|---|---|---|---|
| | EEG hypoxia tolerance test | | Toxicity |
| Compound of Example | i.p. dose in mg/kg | % change in the EEG-RL | $LD_{50}$ (mouse) in mg/kg |
| 1 | 25 | −50 | i.v.: 135 |
| | | | p.o.: 1190 |
| 5 | 25 | −16 | i.v.: >200 |
| 11 | 50 | −23 | i.v.: 200 |
| 13 | 50 | −32 | i.v.: 200 |
| 14 | 50 | −44 | i.v.: 100–200 |
| 22 | 25 | −38 | i.v.: 50–100 |
| 26 | 25 | −27 | i.v.: 200 |
| 28 | 25 | −12 | i.v.: 100–200 |
| 3-Cyano-2,6-dimethyl-4-(4-thiomorpholinyl)pyridine (Example 13 from German Offenlegungsschrift 2,900,504) | 50 | ±0 | i.p.: 150–300 |
| | 25 | ±0 | |
| 3-Phenoxypyridine (J. Med. Chem. 24, 346–350 (1981)) | 25 | −14 | p.o.: 400–630 |
| Methyl 3-cyano-2,6-dimethyl-4-(2-nitrophenyl)pyridine-5-carboxylate (German Offen-Legungsschrift 3,209,274) | 50 | +16 | i.v.: 50–100 |

It was also possible impressively to confirm the good cerebroprotective action of the compounds according to the invention in other special tests, in which a clear superiority likewise emerged, in this case compared with piracetam (2-oxo-1-pyrrolidineacetamide), which dependent protective action which far exceeded that of the comparison product piracetam.

We claim:

1. A multiply substituted pyridine 1-oxide of the formula I

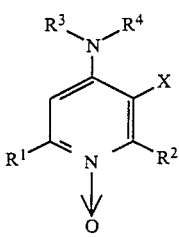

in which
R¹ and R² are, in each case, identical or different and represent alkyl having 1 to 6 carbon atoms,
R³ denotes hydrogen, and
R⁴ denotes mercaptoalkyl having up to 4 carbon atoms, or
R³ and R⁴ form, together with the nitrogen atom in the 4-position, a from the group consisting of a thiomorpholine, morpholine, pyrrolidine, piperidine, hexamethyleneimine, piperazine and homopiperazine ring, whereby the sulfur in the thiomorpholine ring can carry up to tw oxygen atoms, and wherein the second nitrogen in the piperazine or homopiperazine ring is in the form of the NR⁶ group, in which R⁶ is hydrogen, alkyl having up to 2 carbon atoms, phenylalkyl having up to 2 carbon atoms in the alkyl moiety or phenyl, and the phenyl rings in the two latter radicals can carry up to two identical of different substituents from the group consisting of halogen and methoxy, and which heterocyclic ring at its carbon atoms is unsubstituted or carries up to wwo identical or different substituents from the group consisting of hydroxy and alkyl having up to 2 carbon atoms, and
X denotes the cyano or nitro group or the group —CO—R⁵, in which R⁵ represents the amino, hydroxyl or an alkoxy group having up to 4 carbon atoms, or a physiologically tolerated salt of this compound.

2. A compound or its salt as claimed in claim 1, which has at least one of the features that R¹ and R² together contain not more than 8 carbon atoms, that the halogen on the phenyl ring is fluorine, chlorine or bromine, and that the mercaptoalkyl radical in R⁴ contains up to 2 carbon atoms.

3. A compound or its salt as claimed in claim 1 or 2, wherein, in formula 1,
R¹ and R² each has I to 3 carbon atoms,
X denotes the cyano or nitro group, and the group NR³R⁴ represents said thiomorpholine, morpholine, pyrrolidine, piperidine, hexamethyleneimine, piperazine or homopiperazine ring which is unsubstitued or substituted by one alkyl having up to 2 carbon atoms, or represents a 4-phenylpiperazine radical which is unsubstituted or substituted in the phenyl nucleus by one halogen.

4. A compound or its salt as claimed in claim 3, wherein, in formula I,
R¹ and R² each denotes methyl,
X denotes the cyano group, and
NR³R⁴ denotes the thiomorpholine, piperidine or hexamethyleneimine ring.

5. A compound or its salt as claimed in claim 4, which is 3-cyano-2,6-dimethyl-4-(4-thiomorpholinyl)phridine 1-oxixe.

6. A pharmaceutical composition comprising an amount effective for use as a pharmaceutical in the therapy of a mammal of (a) at least one compound of the formula I as claimed in claim 1, or (b) a physiologically tolerated salt thereof, or a combination of (a) and (b), in combination with a pharmaceutically acceptable carrier.

7. A pharmaceutical composition as claimed in claim 6 for the prevention and treatment of brain disorders caused by vascular and degenerative factors, and in the form of solid dosage units containing up to 1000 mg, or in the form of injection solutions in ampoule from containing up to 200 mg.

8. A method for the preparation of medicaments for the prevention and treatment of brain disorders caused by vascular and degnerative factors which comprises incorporating in said medicaments (a) multiply substituted pyridine 1-oxides of the formula I as claimed in claim 1, or (b) their physiologically tolerated sales, or (c) a combination of (a) and (b).

9. A method for the treatment of patients suffering from brain disorders caused by vascular and degenerative factors, which comprises administration to these patients of an effective amount for said treatment of a medicament as claimed in claim 6.

10. The method as claimed in claim 9, wherein the medicament is administered orally in a dose of 100–2000 mg of active compound, or intravenously in a dose of 5 to 500 mg of active compound.

11. The method as claimed in claim 9, wherein the medicament is administered orally in a dose of 300–900 mg of active compound, or intravenously in a dose of 20–200 mg of active compound.

12. The pharmaceutical composition as claimed in claim 7 in the form of solid dosage units containing from 100 to 300 mg, or in the form of injection solutions in ampoule form containing 20 to 100 mg.

13. The compound or its salt as claimed in claim 3 wherein, in formula I, R¹ and R² each represents methyl.

* * * * *

UNITED STATES PATENT AND TRADEMARK OFFICE
CERTIFICATE OF CORRECTION

PATENT NO. : 4,859,663
DATED : August 22, 1989
INVENTOR(S) : Wilfried Greve et al It is certified that error appears in the above-identified patent and that said Letters Patent is hereby corrected as shown below:

Title page, Abstract, 3rd to the last line change "whcich" to --which--.

Claim 1, column 17, line 19, "a" (1st occurrence) should be followed by --heterocyclic ring--.

Claim 1, column 17, line 20, change "morpholine" to --morpholine--.

Claim 1, column 17, line 23, change "tw" to --two--.

Claim 1, column 17, line 33, change "wwo" to --two--.

Claim 3, column 17, line 49, change "I" to --1--.

Claim 5, column 18, line 11, change "phridine" to --pyridine--.

Claim 5, column 18, line 12, change "oxixe" to --oxide--.

Claim 8, column 18, line 31, change "sales" to --salts--.

Signed and Sealed this

Second Day of October, 1990

*Attest:*

HARRY F. MANBECK, JR.

*Attesting Officer*   *Commissioner of Patents and Trademarks*